(12) United States Patent
Chen et al.

(10) Patent No.: US 7,078,472 B2
(45) Date of Patent: Jul. 18, 2006

(54) BICARBOXYL MONOMERS, COPOLYMERS AND PREPARATION PROCESS OF THE SAME

(75) Inventors: Lung-Pin Chen, Tainan (TW); Kung-Chung Hsu, Taipei (TW)

(73) Assignee: National Taiwan Normal University, Taipei (TW)

( * ) Notice: Subject to any disclaimer, the term of this patent is extended or adjusted under 35 U.S.C. 154(b) by 305 days.

(21) Appl. No.: 10/736,639

(22) Filed: Dec. 17, 2003

(65) Prior Publication Data

US 2004/0127624 A1    Jul. 1, 2004

(30) Foreign Application Priority Data

Dec. 31, 2002    (TW) .............................. 91138143 A (51) Int. Cl.
    *C08F 120/10*    (2006.01)
(52) U.S. Cl. .............................. 526/318.2; 526/307.3; 526/307.4
(58) Field of Classification Search ............. 526/307.3, 526/307.4, 318.2
    See application file for complete search history.

(56) References Cited

OTHER PUBLICATIONS

Chen et al. Jorunal of Applied Polymer Science (2005), 98(1), 109-115.*

* cited by examiner

*Primary Examiner*—Helen L. Pezzuto
(74) *Attorney, Agent, or Firm*—Bacon & Thomas, PLLC (57) ABSTRACT

The present invention relates to a bicarboxyl monomer of formula (I), $$\underset{OR_1}{\underset{|}{O=C}}\overset{HC=CH}{\diagup\diagdown}\underset{NH-\underset{\|}{C}-OR^2}{\underset{|}{C=O}}\overset{O}{} \quad (I)$$

wherein $R_1$ and $R_2$ independently is H, alkali metal, or $NH_4$. A dispersant composition containing copolymer made from monomer (I) is also disclosed. The copolymer can be applied to prepare ceramic powder slurry for reducing the release of cations, dispersing the ceramic particles homogenously in the ceramic powder slurry, as well as stabilizing the suspension in the ceramic powder slurry.

6 Claims, 6 Drawing Sheets

BICARBOXYL MONOMERS, COPOLYMERS AND PREPARATION PROCESS OF THE SAME

BACKGROUND OF THE INVENTION

1. Field of the Invention

The present invention relates to a bicarboxyl monomer, copolymer and their preparing process and, more particularly, to a dispersant suitable for processing a ceramic powder suspension.

2. Description of Related Art

Titanate-based ceramic powders such as barium titanate and lead zirconium titanate powders have been applied in manufacturing various electric devices (e.g. capacitors, inductors, or piezoelectric sensors). For the applications mentioned above, the slurry of titanate-based ceramic materials or powders has to be prepared first. Normally, the slurry is prepared by adding titanate-based ceramic powder (e.g. barium titanate powder) into a solvent. The solvent used for the slurry can be either organic or water-based. Owing to safety, economic, and environmental concerns, the preparation of water-based slurries has currently been preferred.

It is clear that the preparation of a well-dispersed or stable aqueous slurry of ceramic powder is an important issue in the ceramic industry. The dispersibility of ceramic powder in aqueous suspension is well-known to be highly related to the quality of the corresponding sintered products. For example, the barium titanate slurries with poor dispersion cannot form a uniform microstructure, which leads to a lower green packing density and poor electrical properties of the sintered product. In order to obtain good quality of the sintered ceramic products, a dispersant is usually added to the ceramic slurry before further manufacturing process.

For the aqueous titanate-based ceramic slurry, ammonium polymethacrylate, known as Darvan C commercially, is commonly used as a dispersant. Besides, the dispersion of other ceramic particles, e.g. aluminum oxide, zirconium oxide or titanium nitride, in aqueous solution also uses Darvan C as a dispersant. Although the dispersing effectiveness of Darvan C is acceptable, improvement is still required. For example, a high level of leached barium ions is found in barium titanate slurry when Darven C was used as a dispersing agent, which may cause abnormal grain growth and formation of inhomogeneous microstructure. Moreover, the effectiveness of Darvan C toward dispersing barium titanate powder with small particle size, especially in a nanometer level, remains to be examined. Finally, owing to the trend of miniaturization of electronic parts or devices, the traditional processes for the related ceramic slurry need to be modified or even reformed. Meanwhile, the dispersion of ceramic particles in slurries needs to be improved further.

The present invention is to provide a bicarboxyl monomer, copolymer and their preparing process to mitigate and/or solve the aforementioned problems.

SUMMARY OF THE INVENTION

The object of the present invention is to provide bicarboxyl monomers and copolymers based on bicarboxyl monomers, and their preparation methods for reducing the release of cations (e.g. barium ions), dispersing the ceramic particles homogenously in the ceramic powder slurry (e.g. barium titanate slurry), as well as stabilizing the suspension in the ceramic powder slurry (e.g. barium titanate slurry).

Another object of the present invention is to provide bicarboxyl monomers and copolymers based on bicarboxyl monomers and the preparation methods of the same, so as to prepare ceramic materials (e.g. titanate-based ceramic materials) with high dielectric constant and low dielectric loss.

Still another object of the present invention is to provide a polymeric dispersant composition for preparing aqueous slurries with ceramic powders such as barium titanate, aluminum oxide or zirconium oxide homogeneously dispersed.

To achieve the object, the bicarboxyl monomer of the present invention is of formula (I), wherein $R_1$ and $R_2$ independently is H, alkali metal, or $NH_4$.

The process for preparing a bicarboxyl monomer of the present invention mainly comprises the following steps. First, an organic solution containing maleic anhydride is provided (step a) and ammonium carbamate is then added to said organic solution (step b). Next, said organic solution is heated to form a precipitate ((step c). After filtrating said solution (step d), the obtained precipitate is then dissolved in water and its pH value is adjusted to a range between 9 to 11 (step e). Finally, the excessive solvent is removed and said precipitate is dried to become a bicarboxyl monomer (step f).

The bicarboxyl copolymer of the present invention is as formula (II):

wherein $R_1$ and $R_2$ is independently H, alkali metal, or $NH_4$; m is an integral from 10 to 5000; and n is an integral from 10 to 3000.

The process for preparing a bicarboxyl copolymer of the present invention mainly comprises the following steps. An aqueous solution (1) containing ammonium 4-carboxylamino-4-oxo-2-butenate and acrylamide, and an aqueous solution (2) containing potassium persulfate and sodium thiosulfate are provided, wherein the molar ratio of ammonium 4-carboxylamino-4-oxo-2-butenate to acrylamide in solution (1) ranges from 1:0.1 to 1:10, and the molar ratio of potassium persulfate to sodium thiosulfate in solution (2) ranges from 3:1 to 7:1 (step a). Next, solution (2) is added to solution (1) to form a mixture and said mixture is then sealed to stand for 5 to 100 hours to form a copolymer of 4-carboxylamino-4-oxo-2-butenate/acrylamide (PCOB) (step b).

The copolymer composition of the present invention, comprising the copolymers aforementioned, serves as a dispersant composition for a ceramic powder suspension.

Other objects, advantages, and novel features of the invention will become more apparent from the following detailed description when taken in conjunction with the accompanying drawings.

DETAILED DESCRIPTION OF THE PREFERRED EMBODIMENT

In the present invention, $R_1$ and $R_2$ of formula (I) or (II) independently can be H, alkali metal, or $NH_4$. Preferably $R_1$ and $R_2$ of formula (I) or (II) independently is H, sodium or potassium. In the process for preparing bicarboxyl monomer of the present invention, the organic solvent can be any conventional organic solvent. Preferably the organic solvent is ketone, alcohol, or ether. More preferably, the organic solvent is acetone. The concentration of maleic anhydride of the organic solution in step (a) can be any concentration less than 50 wt %. Preferably, the concentration of maleic anhydride of the organic solution in step (a) ranges from 12 wt % to 25 wt %. The concentration of ammonium carbamate in the organic solution in step (b) can be any concentration less than 40 wt %. Preferably, the concentration of ammonium carbamate in the organic solution in step (b) ranges from 10 wt % to 20 wt %. The heating temperature in step (c) can be any temperature less than 100° C. Preferably, the heating temperature in step (c) ranges from 40 to 60° C. The pH value of said solution in step (e) can be adjusted by any conventional means. Preferably, the pH value of said solution is adjusted by adding ammonium hydroxide of a concentration ranging from 0.5 to 1.5 N.

In the process for preparing the bicarboxyl copolymer of the present invention, the molar ratio of potassium persulfate to sodium thiosulfate in solution (2) ranges from 3:1 to 7:1. Preferably, the molar ratio of potassium persulfate to sodium thiosulfate in solution (2) ranges from 4:1 to 6:1. In addition, the molar ratio of ammonium 4-carboxylamino-4-oxo-2-butenate to acrylamide in solution (1) ranges from 1:0.1 to 1:10. Preferably, the molar ratio of ammonium 4-carboxylamino-4-oxo-2-butenate to acrylamide in solution (1) ranges from 1:1 to 1:6. The duration for being sealed and standing in step (b) is 5 to 100 hours, and preferably 30 to 85 hours. The copolymer composition of the present invention serves as a dispersant composition for all ceramic powder suspension. Preferably, the copolymer composition of the present invention is suitable for preparing the slurry containing barium titanate, aluminum oxide, or zirconium oxide.

In the embodiments of the present invention, the maleic acid, acetone, ammonium carbamate, ammonium hydroxide, acrylamide, potassium persulfate, sodium thiosulfate, and Darvan C are obtained by well-known arts. Similarly, the operation of $H^1$-NMR and IR in the following embodiments is also achieved according to well-known arts.

Embodiment 1

Preparation of 4-carboxylamino-4-oxo-2-butenate

Maleic acid (14.2 g) in acetone (80 g) is added with ammonium carbamate (15.6 g) and is reacted at 50° C. for 2 hours. The solvent is then removed by filtering. The filtered precipitate is washed by acetone twice and further dried in a vacuum oven at room temperature for 1 day.

Figure 1:
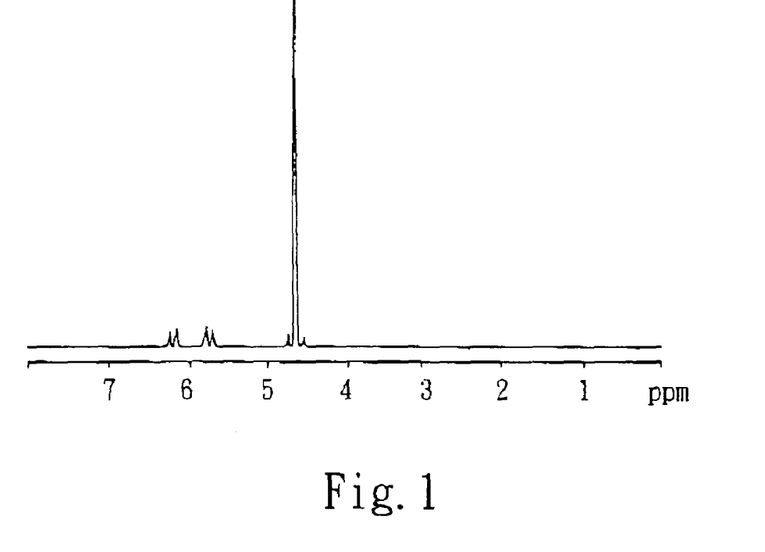
FIG. 1 is the $H^1$-NMR spectrum of PCOB monomer of the present invention.
Figure 2:
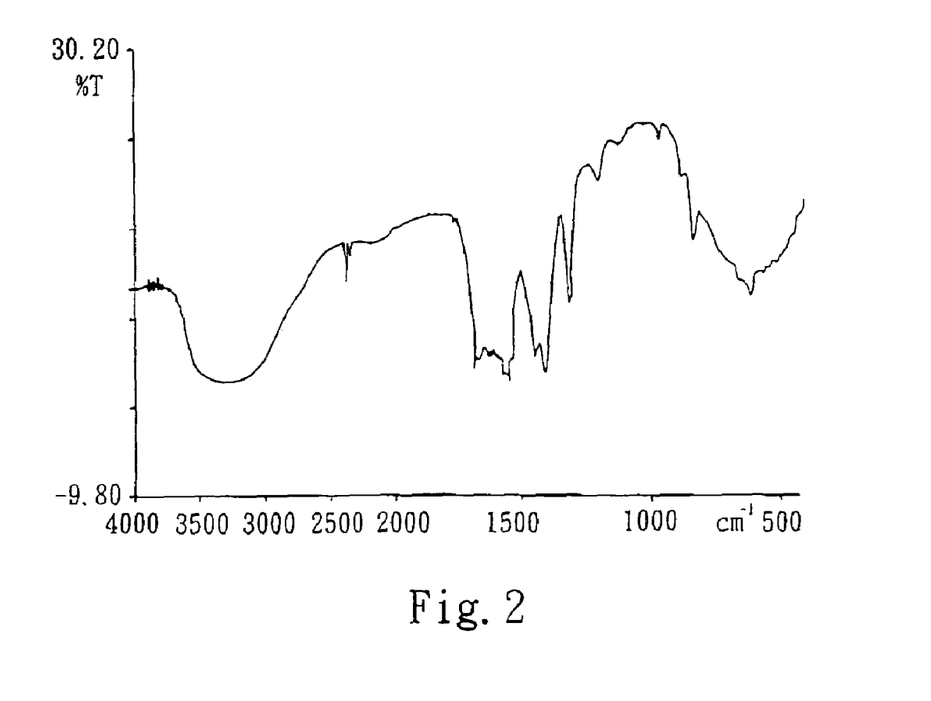
FIG. 2 is the IR spectrum of PCOB monomer of the present invention.

The precipitate (20 g) is dissolved in deionized water and the pH of the solution is adjusted to 10 by adding adequate amount of 1 N aqueous ammonium hydroxide. After that, the solution is stirred at room temperature for about 1 hour. The solvent is then removed by filtering. The filtered precipitate is washed by acetone twice and further dried in a vacuum oven at room temperature for 1 day. A solid product of 18.6 g is obtained. According to the $H^1$-NMR and IR spectra (FIG. 1 and FIG. 2), the product is identified as 4-carboxylamino-4-oxo-2-butenate.

Embodiment 2

Preparation of 4-carboxylamino-4-oxo-2-butenate/acrylamide Copolymer (PCOB)

Figure 3:
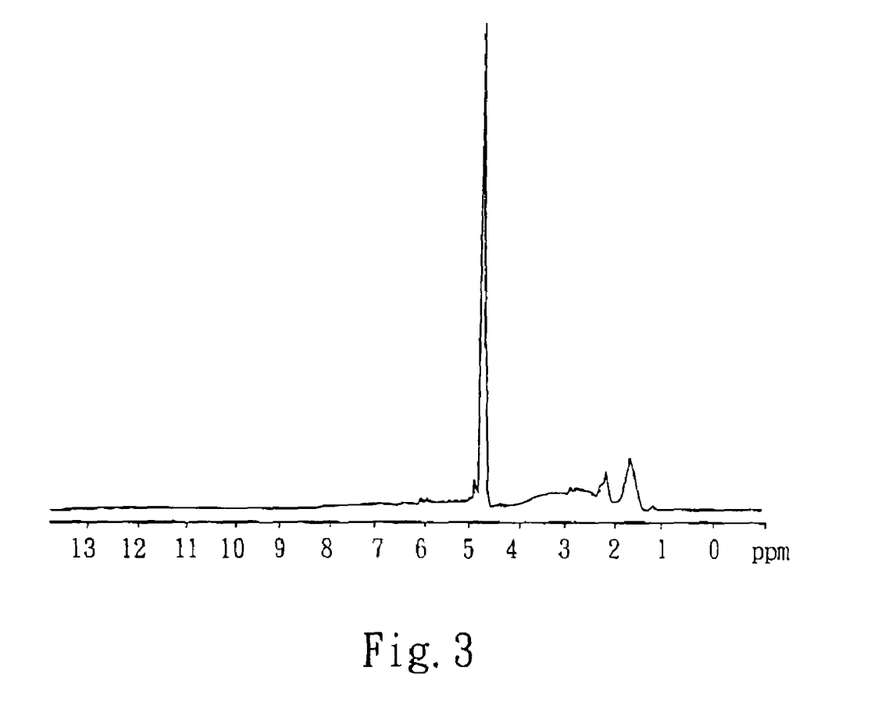
FIG. 3 is the $H^1$-NMR spectrum of PCOB of the present invention.
Figure 4:
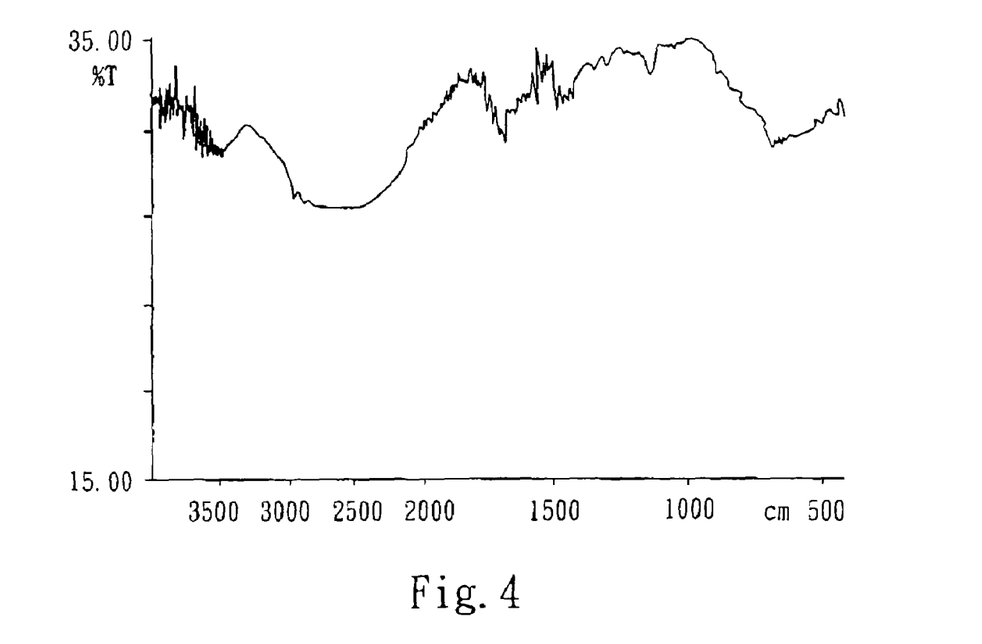
FIG. 4 is the IR spectrum of PCOB of the present invention.

Ammonium 4-carboxylamino-4-oxo-2-butenate (7.72 g) and acrylamide (28.4 g) are dissolved in deionized water (144 g) under a nitrogen gas stream for 10 minutes to form solution (1). A solution (2) is prepared by dissolving potassium persulfate (4.28 g) and sodium thiosulfate (0.856 g) in deionized water (36 g) under a nitrogen gas stream for 10 minutes. Solution (2) is added to solution (1), and stirred for a few minutes. The mixture is then sealed for 3 days. After that, the solvent is then removed by filtering. The filtered precipitate is washed by acetone twice and further dried in a vacuum oven at room temperature for 1 day. A solid product of 178 g is obtained. According to the $H^1$-NMR and IR spectra (FIG. 3 and FIG. 4), the product is identified as 4-carboxylamino-4-oxo-2-butenate/acrylamide copolymer (PCOB).

Particle Size of Barium Titanate Slurry

The dispersing effectiveness of the dispersant of the present invention and that of a commercial dispersant, i.e., Darvan C (provided from S. T. Vanderbilt Inc.), in barium titanate slurry is examined and compared. The barium titanate powder used herein has particle size in a micron level, which is provided by Prosperity Dielectrics Inc.

Each dispersant is individually dissolved in deionized water. Then barium titanate powder is added to each dispersant solution. The slurry with no dispersant present is also prepared by the same procedure without addition of any dispersant. The pH of all barium titanate solutions is adjusted to 12 by a solution of 1N NaOH. The weight ratio of dispersant to barium titanate powder is 1:100 while the weight ratio of water to barium titanate powder is 4:1. The sample is then ball-milled for 24 hours, and the particle size is measured by a laser particle size analyzer (Mastersizer 2000, Malvern, UK).

Figure 5:
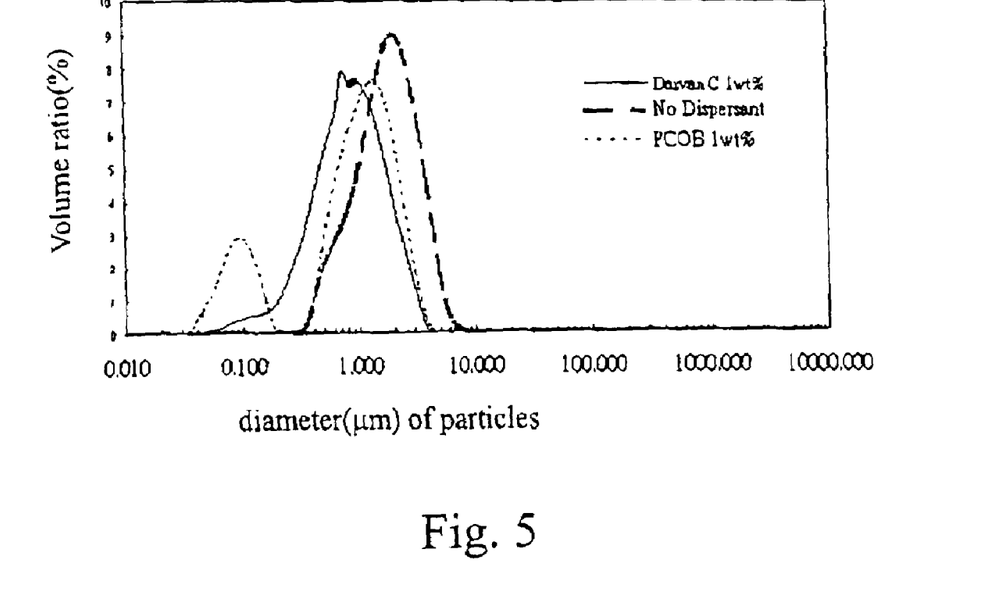
FIG. 5 is a diagram showing the particle size distribution of the barium titanate slurry after adding various dispersants.

FIG. 5 is a diagram showing the particle size distribution of the barium titanate slurry after adding various dispersants. The average particle size ($D_{50}$) of the slurry with no dispersant present is about 1.69 micron. In contrast, the average particle size ($D_{50}$) of the slurry added with 4-carboxylamino-4-oxo-2-butenate/acrylamide copolymer (PCOB) dispersant is about 0.95 micron, which is less than that of the slurry without the presence of any dispersant, and is close to that of the slurry added with Darven C dispersant. This result suggests that PCOB provides dispersion to the barium titanate particles.

Figure 6:
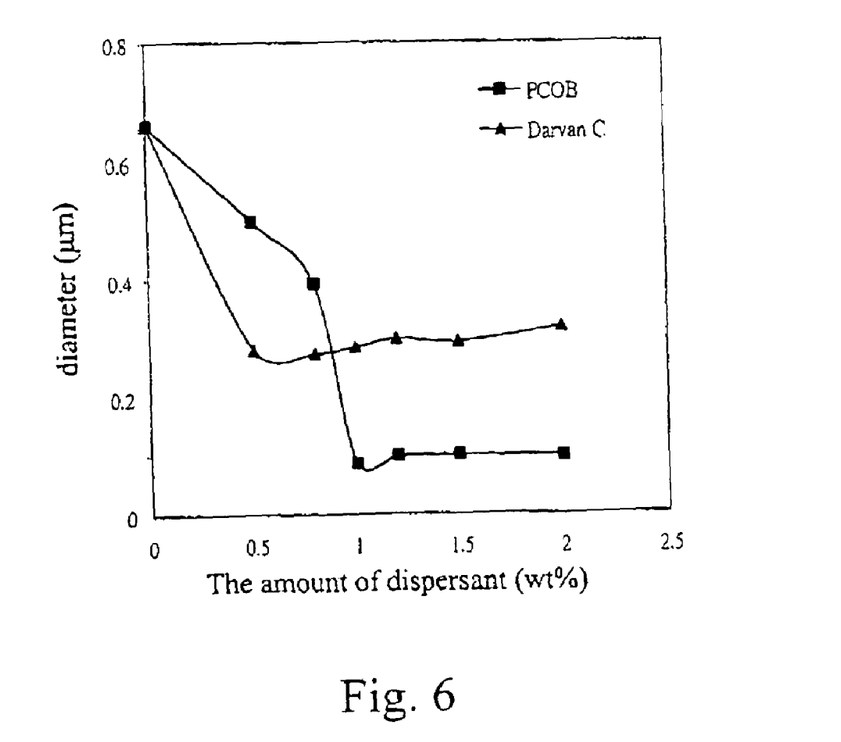
FIG. 6 is a diagram showing the particle size ($D_{10}$) of the barium titanate slurry after adding various amounts of dispersant.

FIG. 6 is a diagram showing the particle size ($D_{10}$) of the barium titanate slurry after adding various amounts of dispersant. According to FIG. 6, the minimum particle size ($D_{10}$) is about 0.085 micron when 1 wt % of PCOB is added. For Darvan C, the minimum $D_{10}$ is about 0.28 micron when 0.8 wt % of Darvan C is added. These results indicate that PCOB provides a better dispersion to the smaller size of barium titanate particles. Since smaller size powder particles can fill the spaces between the larger particles, the packing density is higher.

Dielectric Constant and Dielectric Loss of Barium Titanate Sample

In order to confirm the powder particles formed according to the present invention can be more densely packed, the dielectric constant and dielectric loss of the barium titanate sample are measured. The ceramic sample is formed after the barium titanate slurries either having the dispersant of the present invention or the commercial dispersant Darvan C (provided from S. T. Vanderbilt) added is subjected to drying, grinding, compacting, sintering, silver plating, and thermal treatment. The results of the measurements are shown in Tables 1 and 2.

Table 1 shows the dielectric constant of barium titanate sample having various dispersants added at different sintering temperatures. As shown in Table 1, under different sintering temperatures, the dielectric constant of the sintered ceramic sample having PCOB of the present invention added as a dispersant is higher than that having Darvan C added. Therefore, adding PCOB as a dispersant provides a better dispersion, and the particles can be more densely packed to increase the dielectric constant of the sample after sintering. Table 2 shows the dielectric loss of barium titanate sample having various dispersants added at different sintering temperatures. As shown in Table 2, under different sintering temperatures, adding PCOB as a dispersant results in a lower dielectric loss.

TABLE 1 the dielectric constant of barium titanate samples having various dispersants added at different sintering temperatures.

| | 1200° C. | 1300° C. | 1400° C. |
|---|---|---|---|
| PCOB | 2000 | 2150 | 1750 |
| Darvan C | 1700 | 1950 | 1230 |

TABLE 2 the dielectric loss of barium titanate samples having various dispersants added at different sintering temperatures.

| | 1200° C. | 1300° C. | 1400° C. |
|---|---|---|---|
| PCOB | 0.023 | 0.015 | 0.018 |
| Darvan C | 0.039 | 0.037 | 0.014 |

Viscosity of Barium Titanate Slurry

The viscosity of barium titanate slurry with various amounts of the dispersant of the present invention is measured. The viscosity of barium titanate slurry with various amounts of Darvan C is also measured here.

Slurry is prepared by mixing barium titanate powder and deionized water with a weight ratio of 3:2. The weight ratios of dispersant to barium titanate powder are 0.3:100, 0.5:100, 0.8:100, 1:100, and 1.5:100, respectively. The pH of the slurry is then adjusted to about 12. After ball-milling the slurry for 24 hours, the viscosity of the barium titanate slurry having different amounts of dispersant added is measured by a Broodfield DV-II viscometer. The measured results are shown in FIG. 7.

Figure 7:
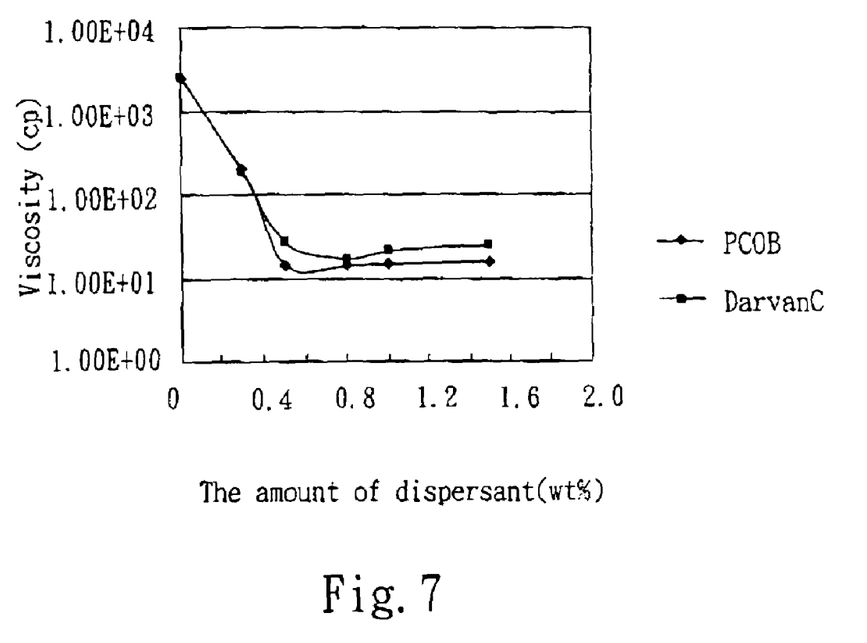
FIG. 7 is a diagram showing the viscosity of the barium titanate slurry after adding various amounts of dispersant.

As shown in FIG. 7, the viscosity decreases to 14.4 cp when PCOB is about 0.5 wt % (weight ratio of dispersant to powder), which demonstrates the viscosity of the barium titanate slurry dramatically decreases after adding PCOB dispersant into the slurry. The result suggests that adding PCOB as a dispersant significantly lower the viscosity of the barium titanate slurry due to better dispersion.

Sedimentation Behavior of Barium Titanate Slurry

To confirm the suspensions prepared according the present invention provide a more desirable dispersing effect, an experiment is conducted by preparing barium titanate powder in deionized water at a weight ratio of about 1:4. The weight ratios of the dispersant to the barium titanate powder are 0:100, 0.5:100, 1:100, 1.5:100, respectively. The pH of the slurry after mixing is adjusted to about 12. After ball-milling the slurry for 24 hours, the barium titanate slurry is poured into a graduated cylinder, sealed and allowed to settle. Changes in the sediment height are observed, and the results are shown in FIG. 8 and FIG. 9.

Figure 8:
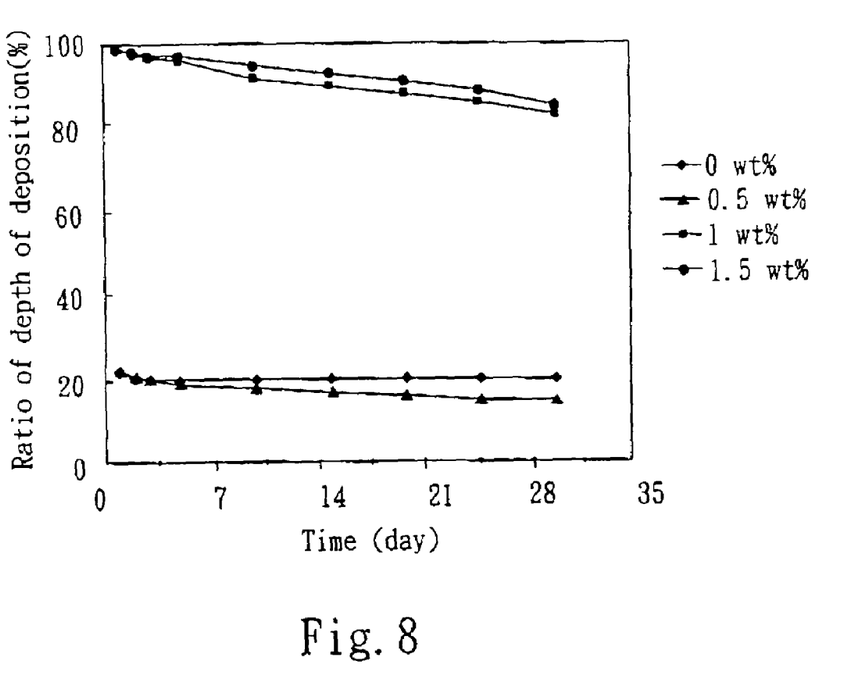
FIG. 8 is a diagram showing the effect of the amount of PCOB on the sediment height of 20 wt % barium titanate slurry.
Figure 9:
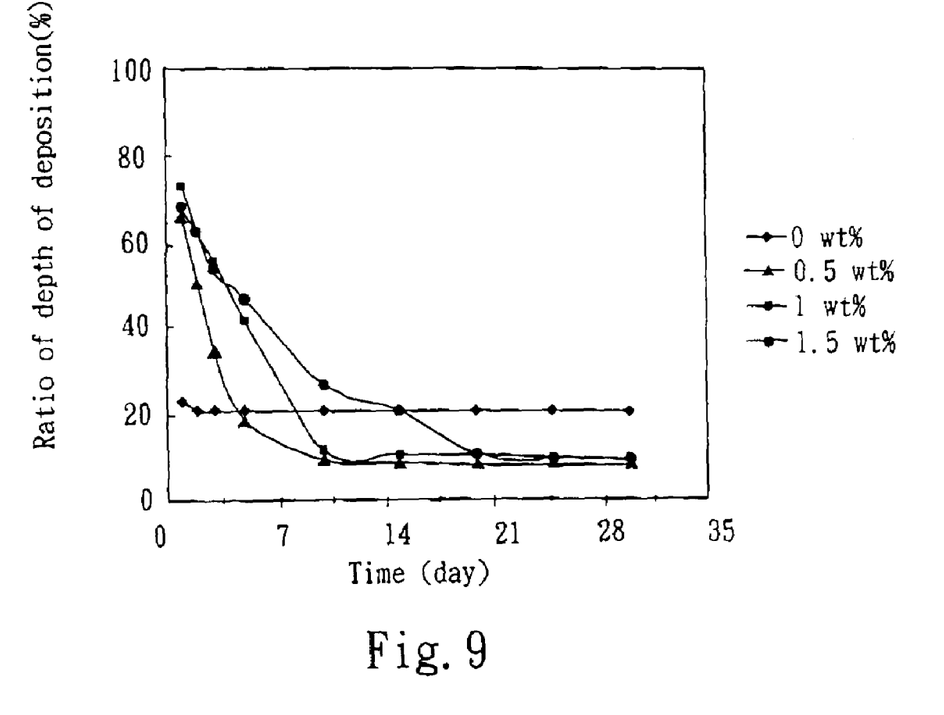
FIG. 9 is a diagram showing the effect of the amount of Darvan C on the sediment height of 20 wt % barium titanate slurry.

FIG. 8 shows the effect of the amount of PCOB on the sediment height of 20 wt % barium titanate slurry. The sediment height refers to the percent of the total height of the dispersion distributed over by the particles. As shown in FIG. 8, when an addition of PCOB is less than 0.5 wt % in the barium titanate slurry, particles would agglomerate and are not well dispersed. Consequently, the sedimentation rate is fast and a majority of the particles are settled within 5 hours. Two layers of water and sediment are easily observed in the graduated cylinder. When the amount of PCOB is greater that 1.0 wt %, the dispersion is good. Most of the barium titanate particles are suspended in the graduated cylinder and very little sediment is present. The suspension in the graduated cylinder appears turbid and no distinguishable layers are observed. FIG. 9 shows the effect of the amount of Davern C on the sediment height of 20 wt % barium titanate slurry. As shown in FIG. 9, when Darven C is added to the barium titanate slurry, sedimentation tends to occur due to the agglomeration of particles. Particles are completely settled to the bottom within about 21 days. Comparing the results in FIG. 8 and in FIG. 9, adding 4-carboxylamino-4-oxo-2-butenate/acrylamide copolymer (PCOB) to the barium titanate slurry as a dispersant definitely improve the dispersion and stability.

Further, using the conventional Darven C as a dispersant for the barium titanate slurry, abnormal grain growth often occurs during the high temperature sintering process due to the dissolution of barium ions. To confirm the present invention can overcome such deficiency, the following experiment is conducted.

Release of Barium Ions in Barium Titanate Slurry

Barium titanate powder and deionized water are provided at a volumetric ratio of 5:95. The weight ratios of the dispersant to the barium titanate powder are 0:100, 0.5:100, 0.8:100, 1:100, 1.2:100, 1.5:100, and 2:100, respectively. The pH value of the slurry is adjusted to about 12. After being ball-milled for 24 hours, the slurry is centrifuged at 10000 rpm for 20 minutes. The supernatant is collected and is measured with an inductive coupling plasma atomic emission spectrum analyzer (ICP-AES, JOBIN YVON JY 24, France). The measured result is shown in FIG. 10.

Figure 10:
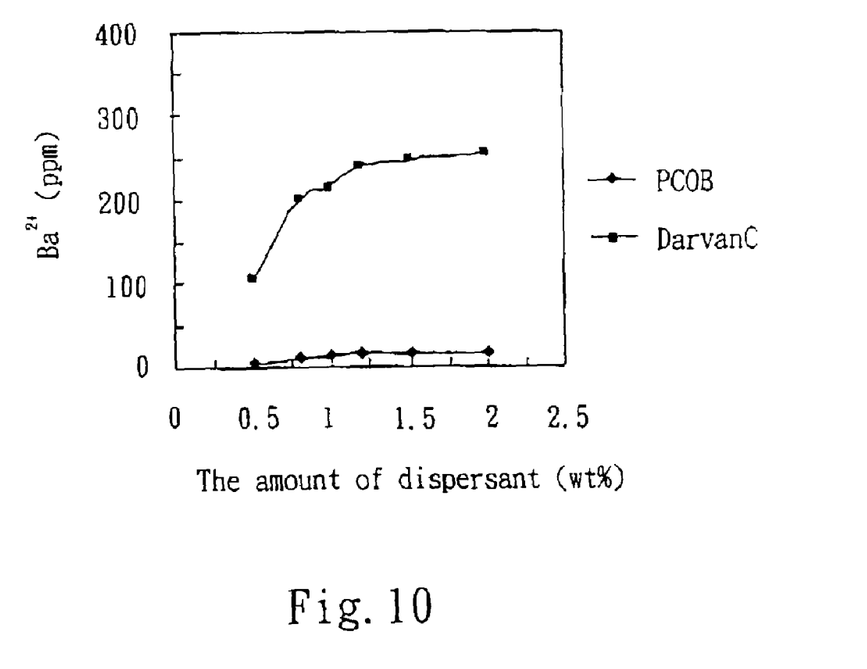
FIG. 10 is a diagram showing the effect of the amount of dispersant on the release of barium ions in the barium titanate slurry.

FIG. 10 shows the relationship between the weight percents of the dispersant added and the amount of the dissolved barium ions. As shown in FIG. 10, when Davern C is used as a dispersant, the amount of barium ions Darven C significantly increases, and the level of barium ions increases with the amount of dispersant. In contrast, when using PCOB as a dispersant, the amount of dissolved barium ions is minimal. This result clearly indicates that adding the novel 4-carboxylamino-4-oxo-2-butenate/acrylamide copolymer (PCOB) dispersant of the present invention to the barium titanate slurry, the dissolution of barium ions is less than that when Darvern C is added to the slurry.

As mentioned earlier, PCOB as a dispersant of the present invention provides good dispersion and significantly reduces the viscosity of the barium titanate slurry. PCOB is also effective in the dispersion of other ceramic powder and greatly decreases the viscosity of the resulting slurry, as illustrated below.

Viscosity of Aluminum Oxide Slurry

The viscosity of aluminum oxide slurry with various amounts of the dispersant of the present invention is measured. The viscosity of aluminum oxide slurry with various amounts of commercial Darvan C dispersant (provided from S. T. Vanderbilt Inc.) is also measured here.

Slurry is prepared by mixing aluminum oxide powder (A16-SG, Alcoa, USA) and deionized water with a weight ratio of 3:7. The average particle size ($D_{50}$) is about 0.4 micron. The weight ratios of dispersant to aluminum oxide powder are 0.1:100, 0.2:100, 0.3:100, and 0.5:100. The pH of the slurry is adjusted to 8. After ball-milling for 24 hours, the viscosity of the aluminum oxide slurry with various amounts of dispersants is measured with a Broodfield DV-II viscometer. The results are shown in FIG. 11.

Figure 11:
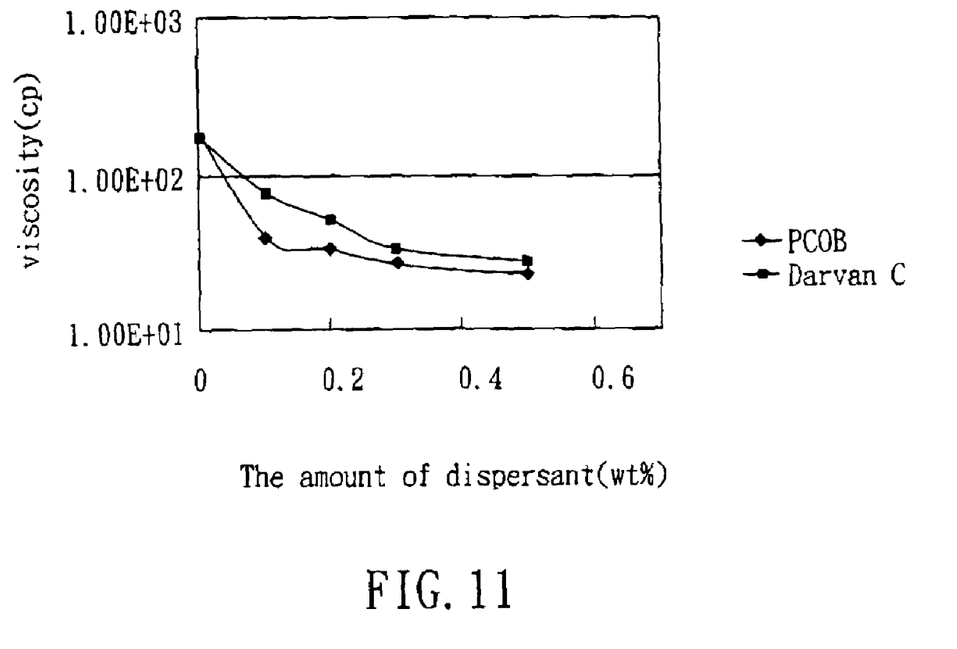
FIG. 11 is a diagram showing the effect of the amount of dispersant on the viscosity of the aluminum oxide slurry.

With reference to FIG. 11, the viscosity decreases to 24 cp when the dispersant amount is 0.5 wt %. It is clear that the viscosity of aluminum oxide slurry dramatically decreases after PCOB dispersant is added.

Viscosity of Zirconium Oxide Slurry

The viscosity of zirconium oxide slurry with various amounts of the dispersant of the present invention is also measured.

Figure 12:
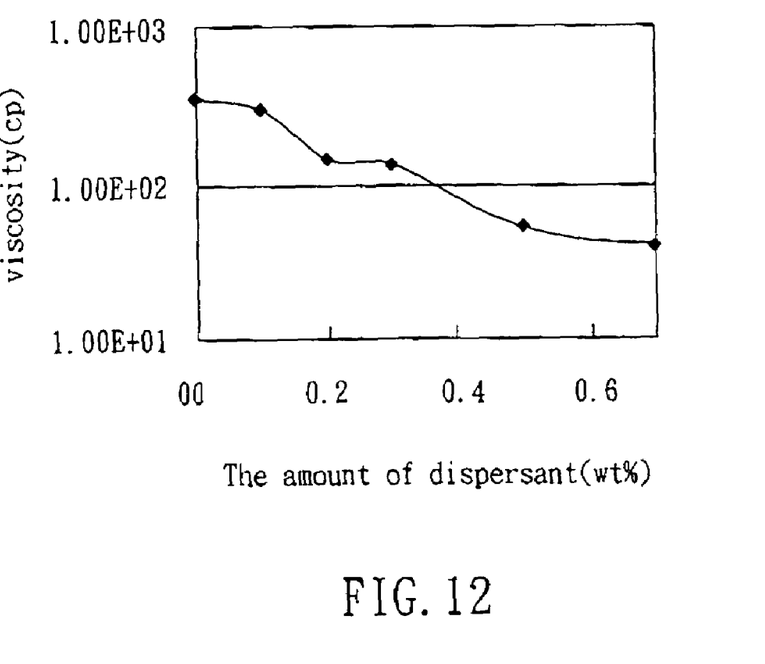
FIG. 12 is a diagram showing the effect of the amount of PCOB on the viscosity of the zirconium oxide slurry.

Slurry is prepared by mixing zirconium oxide powder (TP-3Y, Teamcera, ROC) and deionized water are mixed with a weight ratio of 3:7. The average particle size ($D_{50}$) is about 0.37 micron. In addition, various slurries are made in weight ratios of dispersant to zirconium oxide powder of 0.1:100, 0.2:100, 0.3:100, 0.5:100 and 0.7:100. The pH of the slurry is adjusted to 9. After ball-milling for 24 hours, the relationship between the dispersant amount and the viscosity of each zirconium oxide slurry is analyzed with a Broodfield DV-II viscometer. The results are shown in FIG. 12. According to FIG. 12, the viscosity decreases as the amount of dispersant increases. The viscosity decreases to 40 cp when the concentration of dispersant is 0.7 wt %. The data of viscosity demonstrates that the viscosity of zirconium oxide slurry will decrease when the PCOB dispersant is added.

Although the present invention has been explained in relation to its preferred embodiment, it is to be understood that many other possible modifications and variations can be made without departing from the spirit and scope of the invention as hereinafter claimed.

What is claimed is:

1. A bicarboxyl copolymer of formula (II):

wherein $R_1$ and $R_2$ is independently H, alkali metal, or $NH_4$; m is an integral from 10 to 5000; and n is an integral from 10 to 3000.

2. The bicarboxyl copolymeras claimed in claim 1, wherein said alkali metal is sodium or potassium.

3. The bicarboxyl copolymer as claimed in claim 1, wherein said bicarboxyl copolymer is used to disperse ceramic powder in slurry.

4. The bicarboxyl copolymer as claimed in claim 3, wherein said ceramic powder is barium titanate powder.

5. The bicarboxyl copolymer as claimed in claim 3, wherein said ceramic powder is aluminum oxide powder.

6. The bicarboxyl copolymer as claimed in claim 3, wherein said ceramic powder is zirconium oxide powder.

* * * * *